United States Patent [19]

Malhotra et al.

[11] Patent Number: 5,336,828

[45] Date of Patent: Aug. 9, 1994

[54] HYDROCARBON PROCESSING USING FULLERENE CATALYSTS

[75] Inventors: Ripudaman Malhotra, San Carlos; Doris S. Tse, San Jose; Donald F. McMillen, Menlo Park, all of Calif.

[73] Assignee: SRI International, Menlo Park, Calif.

[21] Appl. No.: 25,502

[22] Filed: Mar. 3, 1993

[51] Int. Cl.$^5$ .............................................. C07C 5/327
[52] U.S. Cl. .................................... 585/654; 585/658
[58] Field of Search ................ 585/654, 658; 423/445, 423/446

[56] References Cited

PUBLICATIONS

Bae, Y. K., et al., "Production, Characterization, and Deposition of Carbon Clusters", Symposium on Clusters and Cluster Assembled Materials: Special Session on Buckminsterfullerene, Boston, Mass., Nov. 29, 1990, published in *The Proceedings of the 1990 Meeting of the MRS Society*, pp. 1–9.

Kratschmer, W., et al., "Solid $C_{60}$: A New Form of Carbon" *Nature*, vol. 347, Sep. 27, 1990, pp. 354–357.

*Primary Examiner*—Asok Pal
*Assistant Examiner*—A. Achutamurthy
*Attorney, Agent, or Firm*—John P. Taylor

[57] ABSTRACT

A process is described for carrying out the dehydrogenation or hydrogenation, including hydrogenolysis, of a hydrocarbon in the presence of one or more soluble fullerene catalysts which have been dissolved in the hydrocarbon (when the hydrocarbon is a liquid capable of dissolving the fullerene catalyst) or dissolved in a solvent which is also a solvent for the hydrocarbon (when the hydrocarbon either is not a liquid or is not a liquid which is a solvent for the fullerene catalyst). The use of a liquid catalyst, i.e., a dissolved fullerene catalyst, inhibits coking reactions to thereby inhibit formation of coke on a solid catalyst or catalyst support by elimination of nucleation points or growth regions for such coke formation.

10 Claims, 2 Drawing Sheets

```
┌─────────────────────────────────────────┐
│  FORMING A SOLUTION OF A SOLUBLE FULLERENE │
│     CATALYST DISSOLVED IN A SOLVENT        │
└─────────────────────────────────────────┘
                    │
┌─────────────────────────────────────────┐
│      CONTACTING A SUBSTITUTED AROMATIC     │
│  HYDROCARBON, IN THE PRESENCE OF HYDROGEN, │
│    WITH THE FULLERENE CATALYST SOLUTION TO │
│    CLEAVE THE SUBSTITUTING MOIETY FROM     │
│           THE AROMATIC RING                │
└─────────────────────────────────────────┘
```

FIGURE 1

```
┌─────────────────────────────────────────┐
│  FORMING A SOLUTION OF A SOLUBLE FULLERENE │
│     CATALYST DISSOLVED IN A SOLVENT        │
└─────────────────────────────────────────┘
                    │
┌─────────────────────────────────────────┐
│    CONTACTING AN UNSATURATED HYDROCARBON   │
│       IN THE PRESENCE OF HYDROGEN, WITH    │
│       THE FULLERENE CATALYST SOLUTION TO   │
│   HYDROGENATE THE UNSATURATED HYDROCARBON  │
└─────────────────────────────────────────┘
```

FIGURE 2

HYDROCARBON PROCESSING USING FULLERENE CATALYSTS

BACKGROUND OF THE INVENTION

1. Field of the Invention

This invention relates to hydrocarbon processing using fullerene catalysts. More particularly this invention relates to the use of fullerene catalysts for dehydrogenation and hydrogenation, including hydrogenolysis (cleavage), of hydrocarbons.

2. Description of the Related Art

Conventional dehydrogenation and hydrogenation reactions with hydrocarbons, including the hydrogenolysis or cleavage of the bond between an alkyl or substituted alkyl group and an aryl group, have involved the use of solid catalysts, such as metal or metal sulfide catalysts, e.g., platinum, nickel, molybdenum, etc., usually formed and carried on a solid support material such as alumina.

However, during such dehydrogenation or hydrogenation reactions, there is a tendency for a coking reaction to also occur when such catalysts are used, with the coke forming on the metal catalyst and/or catalyst support. Apparently such a coking reaction occurs, during the course of the reaction, due to the presence of the solid catalyst/catalyst support materials which can provide catalytic sites, nucleation points, and a quiescent boundary layer for coke formation by the hydrocarbon reactants.

It would, therefore, be preferable to provide a catalyst for such reactions which would be: (a) soluble in the hydrocarbon reactant(s) (when the hydrocarbon is a liquid); or (b) soluble in a solvent in which the hydrocarbon reactant(s) will also dissolve or be dispersible (when the hydrocarbon reactant is not liquid); or (c) soluble in a solvent which will be miscible with the hydrocarbon reactant(s) (when the hydrocarbon reactant is a liquid); or (d) soluble in a solvent which is miscible with a solvent in which the hydrocarbon reactant(s) is dissolved (when the hydrocarbon reactant is a solid).

Such a catalyst, if soluble, would, of course, not need a solid catalyst support, and the absence of both the solid catalyst and the solid catalyst support would eliminate the prior art nucleation source/growth site for coking, or other undesirable side reactions, resulting in higher yields and less contamination of either the reactor or the product.

SUMMARY OF THE INVENTION

It is, therefore, an object of this invention to provide a new method for processing one or more hydrocarbons using a fullerene catalyst for the dehydrogenation or hydrogenation, including hydrogenolysis, of hydrocarbons.

It is another object of this invention to provide a new method for processing one or more hydrocarbons using a soluble fullerene catalyst which will eliminate the need for either a solid catalyst or a solid catalyst support for the dehydrogenation or hydrogenation, including hydrogenolysis, of hydrocarbons.

These and other objects of the invention will be apparent from the following description of the process of the invention.

BRIEF DESCRIPTION OF THE DRAWINGS

FIG. 1 is a flowsheet illustrating a cleavage or hydrogenolysis reaction carried out by the method of the invention.

FIG. 2 is a flowsheet illustrating a hydrogenation reaction carried out by the method of the invention.

DETAILED DESCRIPTION OF THE INVENTION

Figure 3:
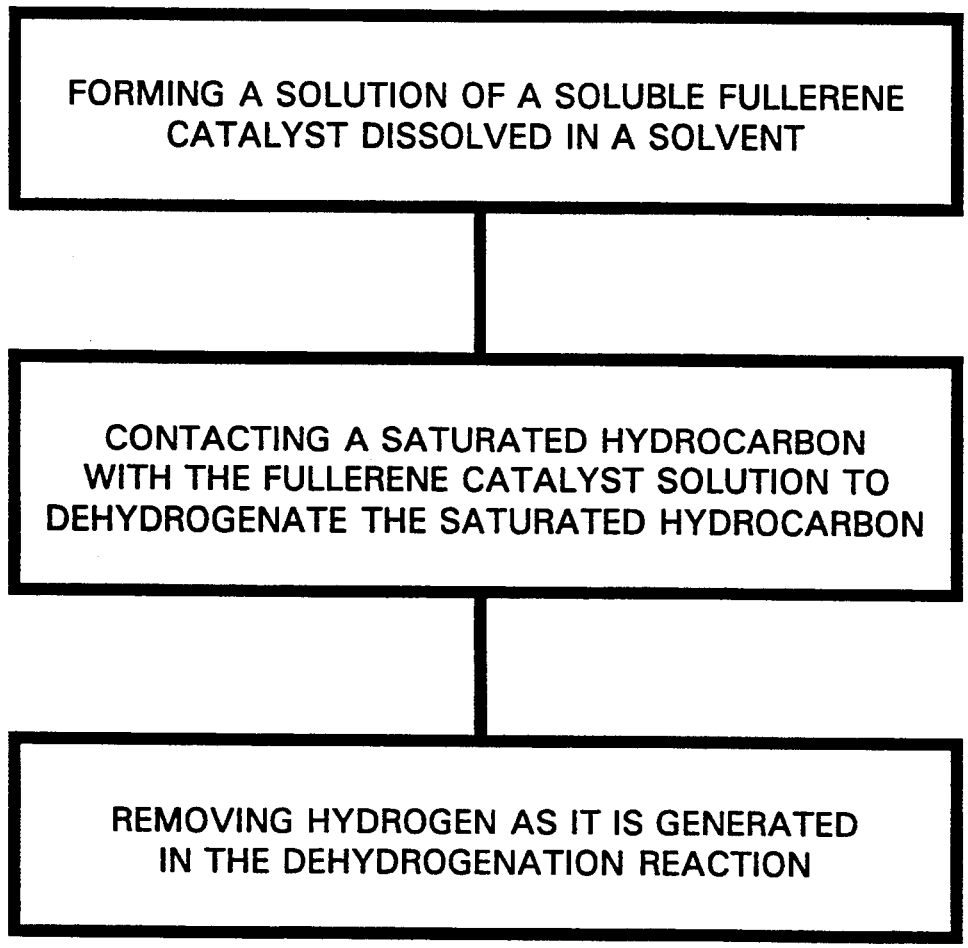
FIG. 3 is a flowsheet illustrating a dehydrogenation reaction carried out by the method of the invention.

The invention comprises a method for carrying out dehydrogenation (removal of hydrogen) and hydrogenation (addition of hydrogen) reactions, including hydrogenolysis reactions (addition of hydrogen involving cleavage) using one or more fullerenes as catalysts. In a preferred embodiment the fullerene catalyst is soluble in the reactants or the solvent in which the reactants are dissolved so that a source of nucleation source/growth sites for coking or other undesirable side reactions is eliminated.

However, the use of solid fullerene catalysts for such reactions should be deemed to be within the scope of the invention. This could include, for example, a soluble fullerene catalyst immobilized on a solid support; a solid fullerene catalyst; a solid mixture of fullerenes and soot produced, for example, during formation of the fullerenes by evaporation of graphite electrodes; or even, in some instances, the soot itself from a process for producing fullerenes.

The method comprises carrying out the dehydrogenation/hydrogenation (including hydrogenolysis) of one or more hydrocarbons in the presence of one or more fullerene catalysts. Preferably the fullerene catalyst is (a) soluble in the hydrocarbon reactant(s) (when the hydrocarbon is a liquid); or (b) soluble in a solvent in which the hydrocarbon reactant(s) will also dissolve or be dispersible (when the hydrocarbon reactant is not liquid); or (c) soluble in a solvent which will be miscible with the hydrocarbon reactant(s) (when the hydrocarbon reactant is a liquid); or (d) soluble in a solvent which is miscible with a solvent in which the hydrocarbon reactant(s) is dissolved (when the hydrocarbon reactant is a solid).

a. The Fullerene Catalyst

The one or more fullerene catalysts useful in the practice of the invention may be further defined as a three dimensional carbon molecule which comprises a clustered carbon structure, generally spherical or spheroidal in shape and having a carbon content generally ranging from about 50 to about 90 carbons, although larger carbon content fullerenes are also known to exist and may be useful in the practice of the invention. These fullerene catalysts are also distinguishable from other carbon forms such as graphite, diamond, or carbon black in that such fullerene catalysts are dissolvable in hydrocarbon solvents such as, for example, toluene and benzene; and they evaporate at much lower temperatures, i.e. $<1000°$ C., than do conventional forms of carbon, e.g., graphite, which sublimes at over $3600°$ C. at ambient pressure.

Such fullerene compounds, as shown in FIG. 1, are known to exist, for example, as $C_{60}$, $C_{70}$, $C_{74}$, $C_{76}$, $C_{78}$, $C_{80}$, $C_{82}$, and $C_{84}$ molecules, with the subscript signifying the number of carbons in the particular fullerene structure. Other fullerenes known to exist and which may be used in the practice of this invention are $C_{86}$, $C_{88}$, and $C_{90}$, and on up by two carbon atoms, e.g., $C_{92}$, $C_{94}$, etc. However, the higher carbon number fullerenes are not as easily obtained by present known methods.

Generally, the one or more fullerene catalysts useful in the practice of the invention may be referred to as one or a mixture of fullerenes having the general formula $C_n$, where n is an even integer from 50 to 120, and preferably from about 60 to about 90.

Formation of these fullerene structures, which are used as catalysts for dehydrogenation and hydrogenation of hydrocarbons practice of the invention, may be by the formation of soot from graphite electrodes followed by evaporation or solvent separation of the fullerenes produced in the soot from the remaining carbon forms therein.

Such formation methods are described, for example, by Kratschmer et al. in "Solid $C_{60}$: A New Form of Carbon", published in *Nature*, Volume 247, pp. 354–357, on Sep. 27, 1990; and by Y. K. Bae et al. in "Production, Characterization, and Deposition of Carbon Clusters", prepared for the Symposium on Clusters and Cluster Assembled Materials Special Session on Buckminsterfullerenes, in Boston, Mass. on Nov. 29, 1990, and published in The Proceedings of the 1990 Meeting of the MRS Society.

The fullerene catalysts useful in the practice of the invention may also be formed and recovered by the method described in copending application Ser. No. 07/814,721, entitled PROCESS AND APPARATUS FOR PRODUCING AND SEPARATING FULLERENES, filed Dec. 24, 1991, and assigned to the assignee of this invention, the disclosure of which is hereby incorporated by reference.

The exact amount of fullerene catalyst used in the dehydrogenation/hydrogenation reaction with one or more hydrocarbons will vary with the particular hydrocarbon reactant(s), the amount of reactant(s), and whether the reaction is to be a batch reaction or a continuous reaction. Usually, however, the amount of fullerene catalyst used will vary from about 1 to about 10 grams of fullerene catalyst per 100 grams of hydrocarbon reactant(s).

The one or more soluble fullerene catalysts may be dissolved in the hydrocarbon reactant(s), when the hydrocarbon is a liquid and the fullerene catalyst is soluble therein. When the hydrocarbon reactant is not a liquid - or is not a solvent for the fullerene catalyst, typical solvents which may be used to dissolve the fullerene catalyst include alkanes such as decalins, haloalkanes such as trichloroethane and tetrachloroethane, and miscellaneous solvents such as methylthiophene and carbon disulfide. The choice of solvent will be governed by the specific reaction conditions employed to effect the reaction. Obviously, the solvent itself should not be subject to any chemical reaction under those conditions, or be derivable as part of a recycle stream.

Preferably, such a solvent will also serve as a solvent for the hydrocarbon reactant, when the hydrocarbon reactant is a solid, or at least be miscible with either the liquid hydrocarbon reactant which is not a solvent for the one or more fullerene catalysts or with a solvent in which the solid hydrocarbon reactant(s) is dissolved.

b. Hydrogenolysis (Cleavage) Reactions

In accordance with one aspect of the invention, the above described fullerene catalysts are used to catalyze a cleavage of a substituted aromatic at the bond between the ring itself and the moiety bonded to the ring. For example, toluene (methyl benzene) can be cleaved into benzene and methane, using a fullerene catalyst in the presence of a source of hydrogen. The general formula for this type of reaction which, in accordance with the invention, is catalyzed with one or more fullerene catalysts, may be written as follows:

(1) 

where Ar is a radical of a 6–30 carbon aromatic ring compound, including, for example, benzene, naphthalene, anthracene, phenanthrene, 1,2,5,6-dibenzanthrene; and M is an aliphatic radical comprising X, R, OR, SR, and NRR′, where X is a halogen other than fluorine, R is a 1–30 carbon alkyl group, and R′ is hydrogen or a 1–30 carbon alkyl group. As will be discussed below, hydrogenation may also occur instead of cleavage. Generally the cleavage reaction will be favored over hydrogenation for multiple ring aromatic compounds, however. Therefore, Ar, in the above formula, is preferably a 10–30 carbon multiple ring aromatic radical. The tendency to remove different substituents on the rings will vary with steric and electronic factors.

The one or more soluble fullerene catalysts are used, in this hydrogenolysis reaction, in an amount which varies from about 1 to 10 parts by weight per 100 parts by weight of the one or more hydrocarbon reactants.

The hydrogenolysis reaction is carried out at a temperature which may vary from about 25° C. to about 500° C. and at a pressure which may vary from about 100 Torr to about 50,000 Torr. The reaction, when carried out as a batch reaction, is usually carried out for a time period which may range from about 1 minute to about 18 hours. When a continuous reaction is carried out, a portion of the reaction mass may be removed continuously from the reactor, the desired cleaved products separated from the remainder of the reaction mass, and the non-cleaved material recycled back to the reactor.

c. Hydrogenation/Dehydrogenation Reactions

In accordance with another aspect of the invention, the above described fullerene catalysts are used to either catalyze the hydrogenation of an aromatic or unsaturated aliphatic (olefinic) hydrocarbon, or the dehydrogenation of a saturated linear, branched, or cycloaliphatic (hydroaromatic) hydrocarbon. Since such reactions are reversible, the presence or absence of hydrogen and temperature will determine whether the hydrogenation or dehydrogenation reaction will predominate.

In its simplest form, the hydrogenation reaction of the invention, using one or more fullerene catalysts, may be illustrated by the following equation, using toluene as an example of the aromatic to be hydrogenated:

(2) 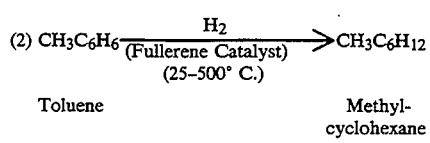

Toluene          Methylcyclohexane

Unsaturated hydrocarbons, both olefinic and aromatic, which may be hydrogenated by the process of the invention, include any unsaturated 2–100 carbon hydrocarbon. Such unsaturated olefinic or aromatic hydrocarbons which may be hydrogenated by the process of the invention include, by way of example, ethene, ethyne, propene, propyne, 2-methyl,1-propene, 1-pentene, 2-pentene, 2-methyl,1-butene, 2-methyl,2-butene, 2,2-dimethyl,1-propene, benzene, naphthalene, anthracene, and phenanthrene.

The one or more soluble fullerene catalysts are used, in the hydrogenation reaction, in an amount which varies from about 1 to 10 parts by weight per 100 parts by weight hydrocarbon reactant. The one or more fullerene catalysts are dissolved in a solvent, which may comprise the unsaturated hydrocarbon reactant itself.

Preferably, as also previously discussed, such a solvent will also serve as a solvent for the unsaturated hydrocarbon reactant, when the hydrocarbon reactant is a solid, or at least be miscible with the liquid hydrocarbon reactant, when the liquid hydrocarbon reactant is not a solvent for the one or more fullerene catalysts.

The hydrogenation reaction is preferably carried out at a temperature which may vary from about 25° C. to about 500° C. and at a pressure which may vary from about 100 Torr to about 50,000 Torr. The hydrogenation reaction, when carried out as a batch reaction, is usually carried out for a time period which may range from about 1 minute to about 18 hours.

In the absence of a source of hydrogen, the dehydrogenation reaction will prevail, as shown in equation (3) illustrated below, using methylcyclohexane as the starting material:

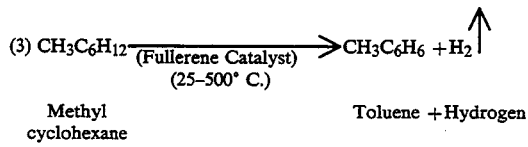

Methyl cyclohexane          Toluene + Hydrogen

Saturated linear, branched, and cyclic hydrocarbons which may be dehydrogenated by the process of the invention may include any 2–100 carbon saturated hydrocarbon. Such saturated linear, branched, and cyclic hydrocarbons which may be dehydrogenated by the process of the invention include, by way of example, ethane, propane, butane, 2-methyl propane, pentane, 2-methyl butane, 2,2-dimethyl propane, hexane, cyclohexane, methyl cyclohexane, dimethyl cyclohexane, etc.

The one or more soluble fullerene catalysts are used, in the dehydrogenation reaction, in an amount which varies from about 1 to 10 parts by weight per 100 parts by weight hydrocarbon reactant. As discussed above, the one or more fullerene catalysts are dissolved in a solvent, which may comprise the saturated hydrocarbon reactant itself.

Preferably, as also previously discussed, such a solvent will also serve as a solvent for the hydrocarbon reactant, when the saturated hydrocarbon reactant is a solid, or at least be miscible with the liquid hydrocarbon reactant, when the liquid hydrocarbon reactant is not a solvent for the one or more fullerene catalysts.

The dehydrogenation reaction is preferably also carried out at a temperature which may vary from about 25° C. to about 500° C. and at a pressure which may vary from about 1 Torr to about 1500 Torr. The dehydrogenation reaction, when carried out as a batch reaction, is usually carried out for a time period which may range from about minute to about 18 hours.

When a continuous hydrogenation or dehydrogenation reaction is carried out, a portion of the reaction mass may be removed continuously from the reactor, the desired product is separated from the remainder of the reaction mass, and the remaining material is recycled back to the reactor. In addition, for a hydrogenation reaction, a source of hydrogen is continuously added to the reactor to drive the reaction toward hydrogenation, while for a dehydrogenation reaction, hydrogen gas must be continuously removed from the reactor as it is generated to continue to drive the reaction toward dehydrogenation.

Thus, for a continuous hydrogenation process, a source of hydrogen and a source of an unsaturated hydrocarbon, i.e., either an aromatic or an unsaturated aliphatic hydrocarbon, are continuously added to the reactor, while product is continuously removed, separated into the desired hydrogenated product and unhydrogenated (unsaturated) hydrocarbon, and the unsaturated hydrocarbons are recycled back to the reactor.

Conversely, for a continuous dehydrogenation process, a source of a saturated hydrocarbon, i.e., either a saturated cyclohydrocarbon or an aliphatic hydrocarbon, is continuously added to the reactor, hydrogen gas, as it is generated, is constantly removed from the reactor, and product is continuously removed, separated into the desired dehydrogenated product and hydrogenated hydrocarbons, and the hydrogenated (saturated) hydrocarbons are recycled back to the reactor.

It should be noted here that none of the above discussed reactions involve the complete reaction of all of the reactants to form the desired product. Rather the reactions are reversible equilibrium reactions wherein the presence of excess hydrogen, or an absence of hydrogen, or a change in temperature shifts the equilibrium to cause a shift in the ratio of products. However, this shift can be both accelerated and enhanced by the use of the fullerene catalysts, in accordance with the invention.

The following examples will serve to illustrate the process of the invention.

EXAMPLE I

To illustrate the cleavage (hydrogenolysis) of 1,2-dinaphthyl methane, equal molar parts of 1,2-dinaphthyl methane and dihydrophenanthrene (the hydrogen source) may be contacted with at least about 5 molar % of a $C_{60}$ fullerene catalyst at a temperature of about 300° C. at ambient pressure for a period of about 2–3 hours. The result will be a mixture of naphthalene, 1-methyl naphthalene, and 2-methyl naphthalene (the cleaved products) and phenanthrene.

EXAMPLE II

To illustrate the hydrogenation of phenanthrene to dihydrophenanthrene, phenanthrene heated to a temperature of about 300° C. at which temperature it is a liquid, was contacted with hydrogen gas at a pressure of about 1000 psi and with about 5 molar % of $C_{60}$ fullerene catalyst for about an hour, with shaking or stirring, as needed, to facilitate mass transfer of the hydrogen from the gas phase to the liquid phenanthrene. The result will be the production of dihydrophenanthrene.

EXAMPLE III

To illustrate the dehydrogenation of dihydrophenanthrene to phenanthrene, dihydrophenanthrene was heated to a temperature of about 300° C. at ambient pressure and contacted with about 5 molar % of $C_{60}$ fullerene catalyst for about an hour. The result will be the production of phenanthrene and the liberation of hydrogen gas.

Thus, the invention provides a new process for processing hydrocarbons which eliminates the need for either a solid catalyst or a solid catalyst support for the dehydrogenation or hydrogenation, including hydrogenolysis, of hydrocarbons by using one or more soluble fullerene catalysts to thereby minimize coking reactions and resultant undesirable coke formation on a solid catalyst or catalyst support.

Having thus described the invention what is claimed is:

1. A process for dehydrogenation of one or more saturated hydrocarbons which comprises:
   a) contacting said saturated hydrocarbon with one or more fullerene catalysts, while maintaining said saturated hydrocarbon at a temperature ranging from about 25° C. to about 500° C. and at a pressure ranging from about 1 Torr to about 1500 Torr to dehydrogenate to said saturated hydrocarbon; and
   b) removing hydrogen from the reaction as it is liberated by said saturated hydrocarbon.

2. The process of claim 1 wherein said one or more fullerene catalysts are soluble in an organic solvent to thereby inhibit coke formation, and said process includes the further step of forming a solution comprising said one or more soluble fullerene catalysts dissolved in said organic solvent.

3. The process of claim 2 wherein said one or more fullerence catalysts have the formula $C_n$, where n is an even integer from 50 to about 120.

4. The process of claim 3 wherein said one or more fullerence catalysts have the formula $C_n$, where n is an even integer from about 60 to about 90.

5. The process of claim 2 wherein said saturated hydrocarbon is a 2-100 carbon saturated hydrocarbon.

6. The process of claim 2 which includes the additional step of separating the dehydrogenated reaction product from the reaction.

7. The process of claim 2 wherein said saturated hydrocarbon is a solid dissolved in a solvent which is miscible with said dissolved fullerene solution.

8. The process of claim 2 wherein said saturated hydrocarbon is a liquid which is miscible with said organic solvent in which said one or more soluble fullerene catalysts are dissolved.

9. The process of claim 2 wherein said saturated hydrocarbon is a liquid which is also the solvent for said one or ore soluble fullerence catalysts.

10. A dehydrogenation process for forming a hydrocarbon product from a different hydrocarbon starting material which comprises contacting with one or more fullerene catalysts a hydrocarbon starting material selected from the group consisting of a saturated aliphatic hydrocarbon, an olefinic hydrocarbon, a cyclic hydrocarbon, an aromatic hydrocarbon, and a substituted aromatic hydrocarbon, while maintaining said hydrocarbon starting material at a temperature ranging from about 25° C. to about 500° C. and at a pressure of at least about 1 Torr, to cause said hydrocarbon starting material to react to form said different hydrocarbon product, with hydrogen removed as it is released from said hydrocarbon starting material during said dehydrogenation reaction.

* * * * *